United States Patent [19]

O'Lenick, Jr.

[11] Patent Number: 5,739,371

[45] Date of Patent: Apr. 14, 1998

[54] CARBOXY SILICONE AMPHOTERIC SURFACTANT COMPLEXES

[75] Inventor: Anthony J. O'Lenick, Jr., Lilburn, Ga.

[73] Assignee: Lambent Technologies Inc., Norcross, Ga.

[21] Appl. No.: 888,891

[22] Filed: Jul. 7, 1997

[51] Int. Cl.$^6$ .................................................. C07F 7/10
[52] U.S. Cl. ..................................................... 556/418
[58] Field of Search .......................................... 556/418

[56] References Cited

U.S. PATENT DOCUMENTS 3,417,136  12/1968  Hovoden .
5,068,377  11/1991  Kawamoto et al. ............... 556/418
5,296,625  3/1994  O'Lenick, Jr. .
5,650,529  7/1997  O'Lenick, Jr. .................... 556/418

*Primary Examiner*—Paul F. Shaver

[57] ABSTRACT

The present invention is directed to a class of compounds that are made by neutralizing the amino group in an amphoteric surfactant with the carboxyllic acid group in a silicone compound. The complex has (a) lower irritation, (b) better foaming properties and (c) improved substantivity to a variety of substrates.

17 Claims, No Drawings

CARBOXY SILICONE AMPHOTERIC SURFACTANT COMPLEXES

FIELD OF THE INVENTION

The present invention is directed to a class of compounds that are made by neutralizing the amino group in an amphoteric surfactant with the carboxyllic acid group in a silicone compound. The complex has (a) lower irritation, (b) better foaming properties and (c) improved substantivity to a variety of substrates.

BACKGROUND OF THE INVENTION

The present invention relates to specific salts of amphoteric surfactants and carboxy silicone polymers. The compounds have unique properties including high foam, detergency and most importantly low irritation to the eye and skin. This makes the compounds of the present invention particularly well suited for personal care applications. Additionally, the compounds of the present invention are useful in industrial applications where detergency and substantivity are required. One particular application is in metal cleaning and corrosion inhibition. The compounds of the present invention provide both detergency and corrosion inhibition when applied to metal surfaces.

Amphoteric surfactants have been known for many years. The amphoteric compounds useful in the preparation of the compounds of the present invention are amino propronates. U.S. Pat. No. 3,417,136 to Hovoden describes the basic technology used to make amphoteric surfactants of the class which is useful for the preparation of the complexes of the present invention.

Silicone carboxy compounds have been described in U.S. Pat. No. 5,296,625 to O'Lenick, incorporated herein by reference.

SUMMARY OF THE INVENTION

The compounds of the present invention are salts of an amphoteric and a carboxy silicone. The preparation of the specific salt compounds of the present invention results in properties heretofore unattainable. Specifically, the fatty amphoteric compounds of the present invention are good detergents, but are somewhat irritating to the skin and eyes. This irritation results in a defatting of the skin and an unacceptable feel on the skin. The silicone carboxylate per se is not a detergent but is very mild to the skin. Together in a salt of the present invention, the compounds of the present invention are very mild to skin and eye, and possess outstanding detergency. This combination of properties make compounds of the present invention applicable in the cleaning of contact lenses. In addition to being very mild, the salts of the present invention do not destroy the breathability of long wear contact lenses. Standard amphoteric surfactants of the class used as a raw material in the preparation of the complexes of the current invention, will clean contact lenses but they will destroy the oxygen permeability of the lenses. The carboxy silicone used as raw materials in the preparation of the complexes of the present invention do not have the desired detergency when used in cleaning contact lenses. Only when the two components are in a specific complex, does the desirable properties of both achieved.

Another very useful application for the salts of the present invention is in two in one shampoos. If one makes a complex of a standard fatty quaternary compound and a standard fatty anionic surfactant, the resulting salt is water insoluble and of very little usefulness in either cleaning or conditioning hair.

The salts of the present invention are water soluble and unexpectedly provide both detergency and conditioning to the hair in a single application.

OBJECT OF THE INVENTION

It is the object of the present invention to provide a series of amphoteric/silicone carboxy salts. These compounds have an outstanding combination of properties making them useful in personal care, and industrial applications. Another aspect of the present invention is a process for using the compounds of the present invention in cleaning and conditioning hair with the application of a single compound.

DETAILED DESCRIPTION OF THE INVENTION

The amphoteric surfactants from which the compounds of the present invention are based have the following structure:

$$R^2-N-(CH_2CH_2C(O)-O^{\ominus}M^{\oplus})_2$$

$R^2$ is selected from the group selected from $CH_3-(CH_2)_a-$ and $CH_3-(CH_2)_b-O-$;

a is an integer ranging from 7 to 19;

b is an integer ranging from 7 to 19;

M is selected from Na, K, and Li.

The nitrogen group in the molecule is a tertiary amine and can be neutralized with a carboxylic acid. Such an acid is the silicone acid useful in the preparation of the compounds of the current invention. The reaction is a neutralization reaction and can be explained by the following reaction sequence:

$$R^2-N-(CH_2CH_2C(O)-O^{\ominus}M^{\oplus})_2 + RC(O)OH \longrightarrow$$
An organic Base    An Organic Acid $$R^2-N^{\oplus}(H)-(CH_2CH_2C(O)-O^{\ominus}M^{\oplus})_2$$
$$RC(O)O^{\ominus}$$
An organic salt The compounds of the present invention are salts which conform to the following structure:

$$A^{\ominus} B^{\oplus}$$

wherein

A is $$R'-\underset{\underset{Me}{|}}{\overset{\overset{Me}{|}}{Si}}-\left[O-\underset{\underset{R}{|}}{\overset{\overset{Me}{|}}{Si}}\right]_o-\left[O-\underset{\underset{R^1}{|}}{\overset{\overset{Me}{|}}{Si}}\right]_q-O-\underset{\underset{Me}{|}}{\overset{\overset{Me}{|}}{Si}}-R'$$

wherein;

Me is methyl;

R and R' are selected from methyl and $-(CH_2)_3-O-(EO)_a-(PO)_b-(EO)_c-C(O)-R''-C(O)-O^-$;

with the proviso that both R and R' are not methyl;

R" is selected from —$CH_2$—$CH_2$—; —$CH_2$—$C(R^7)$-H;

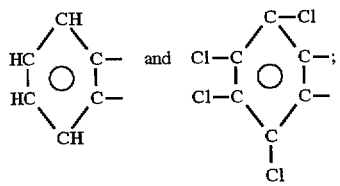

$R^7$ is alkyl having from 1 to 20 carbon atoms;
R
1 is selected from lower alkyl $CH_3(CH)_n$— or phenyl;
n is an integer from 0 to 8;
a, b and c are integers independently ranging from 0 to 20;
EO is —($CH_2CH_2$—O)—;
PO is —($CH_2CH(CH_3)$—O)—;
o is an integer ranging from 1 to 100;
q is an integer ranging from 0 to 500;
and B is

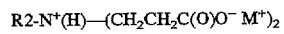

$R^2$ is selected from the group selected from $CH_3$-$(CH_2)_a$— and $CH_3$—$(CH_2)_b$—O—;
a is an integer ranging from 7 to 19;
b is an integer ranging from 7 to 19;
M is selected from Na, K, and Li.

PREFERRED EMBODIMENTS

In a preferred embodiment R2 is $CH_3$—$(CH_2)_a$—.
In another preferred embodiment R2 is $CH_3$—$(CH_2)_b$—O—.
In a preferred embodiment a is 7.
In a preferred embodiment a is 9.
In a preferred embodiment a is 11.
In a preferred embodiment a is 13.
In a preferred embodiment a is 15.
In a preferred embodiment a is 17.
In a preferred embodiment a is 19.
In a preferred embodiment b is 7.
In a preferred embodiment b is 9.
In a preferred embodiment b is 11.
In a preferred embodiment b is 13.
In a preferred embodiment b is 15.
In a preferred embodiment b is 17.
In a preferred embodiment b is 19.

EXAMPLES

Amphoteric Surfactants

$R^2$ is selected from the group selected from $CH_3$—$(CH_2)_a$— and $CH_3$—$(CH_2)_b$—O—;
M is selected from Na, K, and Li;
a is an integer ranging from 7 to 19;
b is an integer ranging from 7 to 19;

CLASS 1

(Alkyl Amphoteric)

R1 is $CH_3$—$(CH_2)_a$—

The amphoteric surfactants of this class are commercially available from a variety of sources including Henkel Corporation. These products are available at a variety of actives. Therefore all were adjusted to 30% actives prior to use. Consequently, the grams listed in the examples for these materials is based upon 30% actives.

| Example | M | a |
|---------|----|----|
| 1 | Na | 7 |
| 2 | K | 9 |
| 3 | Na | 11 |
| 4 | Li | 13 |
| 5 | Na | 15 |
| 6 | K | 17 |
| 7 | Na | 19 |

CLASS 2

(Alkyl ether amphoteric)

Compounds of this class are commercially available from a variety of sources, most importantly Tomah Products of Milton Wis. These products are available at a variety of actives. Therefore all were adjusted to to 30% actives prior to use. Consequently, the grams listed in the examples for these materials is based upon 30% actives.

$R^1$ is $CH_3$—$(CH_2)_b$—O—;

| Example | M | b |
|---------|----|----|
| 8 | Na | 7 |
| 9 | K | 9 |
| 10 | Na | 11 |
| 11 | Li | 13 |
| 12 | Na | 15 |
| 13 | K | 17 |
| 14 | Na | 19 |

Carboxy Silicone Polymers

Carboxy Silicone Polymers are compounds available commercially form Siltech Inc. of Norcross, Ga. and are sold under the Silube tradename. They are the topic of U.S. Pat. No. 5,296,625 to O'Lenick, incorporated herein by reference.

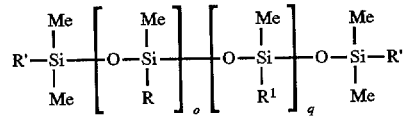

wherein;

Me is methyl;

R and R' are selected from methyl and —$(CH_2)_3$—O—$(EO)_a$—$(PO)_b$—$(EO)_c$—C(O)-R"-C(O)—OH;

with the proviso that both R and R' are not methyl;

R" is selected from —CH$_2$—CH$_2$—; —CH$_2$—C(R$^7$)-H;

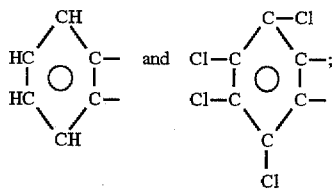

R$^7$ is alkyl having from 1 to 20 carbon atoms;

R1 is selected from lower alkyl CH$_3$(CH)$_n$— or phenyl;

n is an integer from 0 to 8;

a, b and c are integers independently ranging from 0 to 20;

EO is —(CH$_2$CH$_2$—O)—;

PO is —(CH$_2$CH(CH$_3$)—O)—;

o is an integer ranging from 1 to 100;

q is an integer ranging from 0 to 500.

R" Definition

I) O'Lenick Reactant Example I (Succinic Anhydride)

R" is —H$_2$C—CH$_2$—

II) O'Lenick Reactant Example II (Alkyl Succinic Anhydride)

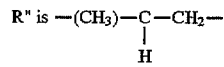

III) O'Lenick Reactant Example III (Alkyl Succinic Anhydride)

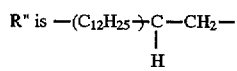

IV) O'Lenick Reactant Example IV (Alkyl Succinic Anhydride)

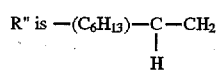

V) O'Lenick Reactant Example V (Alkyl Succinic Anhydride)

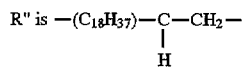

VI) O'Lenick Reactant Example VI (Alkyl Succinic Hydride)

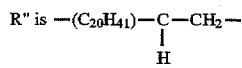

VII) O'Lenick Reactant Example VII (Maleic Anhydride)

VIII) O'Lenick Reactant Example VIII (Phthalic Anhydride)

R" is

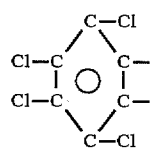

IX) O'Lenick Reactant Example IX (Tetrachlorophthalic Anhydride)

R" is

[structure: tetrachlorophthalic anhydride ring]

| Example | O'Lenick Example (U.S. Pat. No. 5,296,625) |
| --- | --- |
| 15 | 15 |
| 16 | 16 |
| 17 | 17 |
| 18 | 18 |
| 19 | 19 |
| 20 | 20 |
| 21 | 21 |
| 22 | 22 |
| 23 | 23 |
| 24 | 24 |
| 25 | 25 |
| 26 | 26 |
| 27 | 27 |
| 28 | 28 |
| 29 | 29 |
| 30 | 30 |
| 31 | 31 |

EXAMPLES

The compounds of the present invention are prepared by the mixing of the amphoteric surfactant and the carboxy silicone polymer, preferably in aqueous solution, resulting in the neutralization of the compounds and preparation of the salts of the current invention.

Example 32

The 1136.0 grams amphoteric compound at 30% Active (example 1) is added to a suitable vessel. Next 2,429.0 The specified carboxy silicone (example 15) is added under good agitation. 5,667.6 grams of water is then added. The resulting salt is ready to use without additional purification. The compounds can be prepared in aqueous solution if desired by addition of water. Preferred concentrations are between 50% and 30% amphoteric solids by weight.

Note; In the below table Gms. is grams

Examples 33–50

| Example | Carboxy Silicone Compound | | Amphoteric Compound | | Water |
|---|---|---|---|---|---|
| | Example | Grams | Example | Grams | Grams |
| 33 | 15 | 2,429.0 | 1 | 1136.6 | 2429.0 |
| 34 | 16 | 2,147.0 | 2 | 1336.0 | 2147.0 |
| 35 | 17 | 5,398.0 | 3 | 1323.0 | 5398.0 |
| 36 | 18 | 533.0 | 4 | 1310.0 | 533.0 |
| 37 | 19 | 4,723.0 | 5 | 1510.0 | 4723.0 |
| 38 | 20 | 3,083.0 | 6 | 1710.2 | 3083.0 |
| 39 | 21 | 3,648.8 | 7 | 1697.0 | 3648.0 |
| 40 | 22 | 1,722.4 | 8 | 1190.0 | 1722.4 |
| 41 | 23 | 1,288.0 | 9 | 1390.0 | 1288.0 |
| 42 | 24 | 6,100.0 | 10 | 1270.0 | 6100.0 |
| 43 | 25 | 10,115.0 | 11 | 1470.0 | 10115.0 |
| 44 | 26 | 50,269.0 | 12 | 1563.0 | 50269.0 |
| 45 | 27 | 86,185.0 | 13 | 1656.0 | 86185.0 |
| 46 | 28 | 2,645.0 | 14 | 1750.0 | 2645.0 |
| 47 | 29 | 2,372.0 | 1 | 1136.6 | 2372.0 |
| 48 | 30 | 5,229.0 | 2 | 1336.2 | 5299.0 |
| 49 | 31 | 495.6 | 3 | 1323.0 | 495.0 |
| 50 | 32 | 4,695.0 | 4 | 1370.0 | 4695.0 |

APPLICATIONS EXAMPLES

The compounds of the present invention are low irritation surface active agents which exhibit good detergency and foam properties. This combination of properties makes the compounds useful in personal care applications. The following data illustrates the desirable properties of the salts which are lacking in either component alone.

| | Amphoteric Example 1 | Carboxy Silicone Example 22 | Complex Ex 33 |
|---|---|---|---|
| Eye Irritation | Moderate | Mild | Mild |
| Detergency | Good | Poor | Good |
| Foam | Good | Poor | Good |

| | Amphoteric Example 8 | Carboxy Silicone Example 15 | Complex Ex 40 |
|---|---|---|---|
| Eye Irritation | Moderate | Mild | Mild |
| Detergency | Good | Poor | Good |
| Foam | Good | Poor | Good |

What is claimed:

1. A carboxy silicone amphoteric complex which conforms to the following structure:

$$A^\ominus B^\oplus$$

wherein

A is

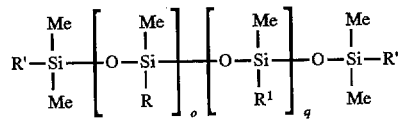

wherein;
Me is methyl;
R and R' are selected from methyl and —$(CH_2)_3$—O—$(EO)_a$—$(PO)_b$—$(EO)_c$—C(O)-R"-C(O)—O⁻;
with the proviso that both R and R' are not methyl;
R" is selected from —$CH_2$—$CH_2$—; —$CH_2$—$C(R^7)$-H;

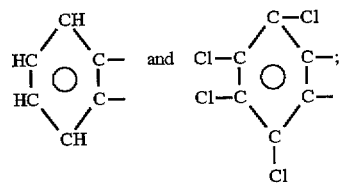

$R^7$ is alkyl having from 1 to 20 carbon atoms;
$R^1$ is selected from lower alkyl $CH_3(CH)_n$— or phenyl;
n is an integer from 0 to 8;
a, b and c are integers independently ranging from 0 to 20;
EO is —$(CH_2CH_2$—O)—;
PO is —$(CH_2CH(CH_3)$—O)—;
o is an integer ranging from 1 to 100;
q is an integer ranging from 0 to 500;
and B is $$R^2\text{-}N^\oplus(H)\text{---}(CH_2CH_2C(O)\text{---}O^\ominus M^\oplus)_2$$

$R^2$ is selected from the group selected from $CH_3$—$(CH_2)_a$— and $CH_3$—$(CH_2)_b$—O—;
a is an integer ranging from 7 to 19;
b is an integer ranging from 7 to 19;
M is selected from Na, K, and Li.

2. A compound of claim 1 wherein R2 is $CH_3$—$(CH_2)_a$—.
3. A compound of claim 1 wherein R2 is $CH_3$—$(CH_2)_b$—O—.
4. A compound of claim 2 wherein a is 7.
5. A compound of claim 2 wherein a is 9.
6. A compound of claim 2 wherein a is 11.
7. A compound of claim 2 wherein a is 13.
8. A compound of claim 2 wherein a is 15.
9. A compound of claim 2 wherein a is 17.
10. A compound of claim 2 wherein a is 19.
11. A compound of claim 3 wherein b is 7.
12. A compound of claim 3 wherein b is 9.
13. A compound of claim 3 wherein b is 11.
14. A compound of claim 3 wherein b is 13.
15. A compound of claim 3 wherein b is 15.
16. A compound of claim 3 wherein b is 17.
17. A compound of claim 3 wherein b is 19.

* * * * *